United States Patent [19]

DiCosimo et al.

[11] Patent Number: 4,861,911
[45] Date of Patent: * Aug. 29, 1989

[54] PROCESS FOR OXIDATION OF BENZENE TO PHENOL PRECURSOR

[75] Inventors: Robert DiCosimo, Shaker Heights; Hsiao-Chiung Szabo, Mentor, both of Ohio

[73] Assignee: The Standard Oil Company, Cleveland, Ohio

[*] Notice: The portion of the term of this patent subsequent to Nov. 8, 2005 has been disclaimed.

[21] Appl. No.: 174,297

[22] Filed: Mar. 28, 1988

Related U.S. Application Data

[63] Continuation of Ser. No. 750,552, Jul. 1, 1985, Pat. No. 4,783,550.

[51] Int. Cl.$^4$ .............................. C07C 67/05
[52] U.S. Cl. ................................... 560/145
[58] Field of Search ........................ 560/145

[56] References Cited

U.S. PATENT DOCUMENTS 4,244,881  1/1981  Giordano et al. ............... 560/131

OTHER PUBLICATIONS

Kochi et al., J. Am. Chem. Soc. 95, pp. 7114–7123, (1973).
Noller, "Chemistry of Organic Compounds", 2nd Ed., pp. 196–198, (1957), 1957.
Hendriks et al., Ind. Eng. Chem. Prod. Res. Dev. 17, pp. 260–264, (1978).
Tang et al., J. Inorg, Nucl. Chem. 35, pp. 3845–3856, (1973).

Primary Examiner—Michael L. Shippen
Attorney, Agent, or Firm—C. S. Lynch; D. J. Untener; L. W. Evans

[57] ABSTRACT

Benzene is oxidized to produce the phenyl ester of a perfluoromonocarboxylic acid by reaction with $H_2O_2$, a perfluoro acid or a combination of acetaldehyde and molecular oxygen, in the presence of (1) a cobalt salt of an organic acid catalyst and (2) a perfluoromonocarboxylic acid solvent.

3 Claims, No Drawings

PROCESS FOR OXIDATION OF BENZENE TO PHENOL PRECURSOR

This is a continuation of co-pending application Ser. No. 750,552 filed July 1, 1985, now U.S. Pat. No. 4,783,550.

This invention relates to the catalytic oxidation of benzene to a precursor of phenol, using a cobalt compound as catalyst.

Kochi and coworkers have reported* the oxidation of benzene with stoichiometric quantities of cobalt (III) trifluoroacetate (2 moles) in trifluoroacetic acid/trifluoroacetic anhydride (TFA-A) to produce phenyl trifluoroacetate. The ester can be hydrolyzed to phenol.

*(a) Kochi, J. K.; Tang, R. T.; Bernath, T. J. Am. Chem. Soc. 1973, 95, 7114–7123. (b) Tang, R., Kochi, J. K. J. Inorg. Nucl. Chem. 1973, 35, 3845–3856.

It is an object of the present invention to provide a catalytic process for oxidizing benzene to an ester precursor of phenol using certain cobalt compounds as catalysts, including the compound used as the stoichiometric cobalt oxidant by Kochi et al.

Another object of the invention is to provide a process for oxidizing benzene to phenol while avoiding using the large amounts of the cobalt compound used by Kochi et al.

Other objects, as well as aspects, features, and advantages, of the invention will be apparent from the disclosure and claims.

These and other objects are realized by the present invention according to which there is provided a process for the catalytic reaction of benzene to produce an ester precursor of phenol by contacting benzene with (a) an oxidant selected from $H_2O_2$, perfluoroperoxyacetic acid, saturated hydrocarbyl percarboxylic acids having 2–12 carbon atoms, and a combination of acetaldehyde and molecular oxygen;

(b) a solvent which is a perfluoroalkylmonocarboxylic acid having 2–6 carbon atoms and zero to 20 volume percent of an anhydride of such a perfluoro acid, based on the volume of the anhydride plus the perfluoro acid used;

(c) as catalyst a Co(II) or Co(III) salt of an organic acid which is soluble in said solvent, said oxidation reaction being effected (1) under substantially anhydrous conditions and (2) at a temperature in the range zero to 50° C., usually 25°–30° C. when $H_2O_2$ or a peracid is the oxidant; and in the range 25°–150° C., usually 60°–80° C., when acetaldehyde plus molecular oxygen is the oxidant, thereby forming the phenyl ester of said perfluoromonocarboxylic acid.

The phenyl ester is of course easily hydrolyzed to phenol and the perfluoromonocarboxylic acid, which can be recycled as solvent to the process.

Examples of the cobalt catalyst include Co(III) acetate, Co(II) acetate, Co(III) benzoate, Co(II) benzoate, Co(III) naphthenate, Co(II) naphthenate, Co(III) trifluoroacetate, Co(II) trifluoroacetate, Co(II) benzene sulfonate and Co(III) benzene sulfonate.

In the foregoing process, however, the actual active cocatalyst species is believed to be Co(III) salt of the perfluoroalkylmonocarboxylic acid, either initially added to the reactor or formed in situ by reaction with a portion of the solvents.

Examples of the defined solvents are $CF_3COOH$, $CF_3CF_2COOH$ and $CF_3CF_2CF_2COOH$.

Usual concentration of the benzene in the reaction mixture of benzene plus solvent is 0.01 to 4M, usually 0.1 to 2M. On the same basis, the concentration of cobalt compound catalyst is usually 0.005 to 0.4 molar.

The amount of catalyst added in the reaction mixture is much less than the stoichiometric amount of 2 moles of the cobalt compound per mole of benzene specified in the prior art. The ratio of moles of cobalt catalyst compound to moles of benzene is usually no more than 0.6/1, and the ratio is usually at least 0.01/1.

In the process of the invention it is preferable to have an anhydride of a defined perfluoroalkylmonocarboxylic acid so that the solvent contains at least 0.05 volume percent anhydride based on the volume of anhydride plus perfluoromonocarboxylic acid charged. The anhydride aids in obtaining and maintaining the essentially anhydrous reaction conditions.

However, when the oxidant is a combination of acetaldehyde and molecular oxygen, it is preferred not to use an anhydride as part of the solvent, or at the most, 2 percent of the volume of the solvent is an anhydride.

When $O_2$ plus acetaldehyde is the oxidant, the concentration of acetaldehyde in the reaction mixture is in the range from 0.002 to 4M. An atmosphere of from 100 to 1200 psia of oxygen gas or air or any mixture thereof is usually used, essentially anhydrous, of course.

The following representative specific examples are not to be taken as limiting. In the examples, the analyses were made by gas chromatography.

EXAMPLE I

To a solution of benzene (0.428 g, 5.49 mmol) and cobalt(II) acetate (0.179 g, 1.01 mmol) in 50 mL of trifluoroacetic acid/10% trifluoroacetic anhydride at 25° C. was added 10 mL of a 0.5M solution of trifluoroperacetic acid in trifluoroacetic acid/10% trifluoroacetic anhydride (cooled to 0° C.) by syringe pump over 20 h with stirring. The reaction mixture was initially a reddish-pink color which turned to dark green-black upon addition of the peracid. After the addition was complete, the reaction mixture was stirred an additional 7 h, then analyzed by gas chromatography using n-octane as an internal standard. The yield of phenyl trifluoroacetate was 56%, with a 58% conversion of benzene (selectivity to phenyl trifluoroacetate=96%). Addition of water to the reaction mixture resulted in the quantitative conversion of phenyl trifluoroacetate to phenol and trifluoroacetic acid solvent.

The example above was repeated without the addition of cobalt(II) acetate to the reaction mixture, and only a 4.6% yield of phenyl trifluoroacetate was obtained.

EXAMPLE 2

A solution of benzene (0.043 g, 0.548 mmol) and cobalt(II) acetate (0.0187 g, 0.106 mmol) in 5 mL of trifluoroacetic acid/10% trifluoroacetic anhydride was stirred at 25° C. and 0.010 mL of 35% peracetic acid (0.052 mmol) and 0.017 mL (0.12 mmol) of trifluoroacetic anhydride added every 30 min. for 10 h. An additional 0.42 g (0.54 mmol) of benzene was added to the solution, and eight more additions of peracetic acid and trifluoroacetic anhydride added before the reaction was analyzed by gas chromatography using n-octane as internal standard. The yield of phenyl trifluoroacetate was 58% with a 65% conversion of benzene (selectivity=89%).

EXAMPLE 3

Into a Parr bomb equipped with glass liner and Teflon-coated magnetic stirring bar was placed cobalt(II) acetate (0.0418 g, 0.236 mmol), benzene (0.0763 g, 0.098 mmol), acetaldehyde (0.044 g, 1.00 mmol), and 10 mL of trifluoroacetic acid. The bomb was pressurized to 1000 psia with oxygen and heated to 60° C. with stirring for 16 h. The yield of phenyl trifluoroacetate was 22.2% with a 63.5% conversion of benzene (selectivity=35%).

EXAMPLE 4

Into a Parr bomb equipped with glass liner and Teflon-coated magnetic stirring bar was placed 0.25 mmol cobalt(II) acetate and 0.22 mmol cobalt(III) acetate, benzene (2.48 mmol), acetaldehyde (2.5 mmol), and 25 mL of trifluoroacetic acid. The bomb was pressurized to 125 psia with oxygen and heated to 60° C. with stirring for 2 h. The yield of phenyl trifluoroacetate was 4.9% with a 21.6% conversion of benzene (selectivity=22.7%).

EXAMPLE 5

Into a Parr bomb equipped with glass liner and Teflon-coated magnetic stirring bar was placed cobalt(III) acetate (0.56 mmol), benzene (2.68 mmol), acetaldehyde (5.0 mmol), and 25 mL of a mixture of 90% of trifluoroacetic acid and 10% trifluoracetic acid anhydride. The bomb was pressurized to 165 psia with oxygen and held at room temperature with stirring for about 64 h. The yield of phenyl trifluoroacetate was 7.3% with a 24.7% conversion of benzene (selectivity=29.6%).

As will be evident to those skilled in the art, various modifications of this invention can be made or followed in the light of the foregoing disclosure and discussion without departing from the spirit and scope of the disclosure or from the scope of the claims.

We claim:

1. A process for the catalytic reaction of benzene which comprises contacting benzene with
    (a) an oxidant selected from $H_2O_2$, perfluoroperoxyacetic acid, saturated hydrocarbyl percarboxylic acids having 2–12 carbon atoms, and a combination of acetaldehyde and molecular oxygen;
    (b) a solvent which is a perfluoroalkylmonocarboxylic acid having 2–6 carbon atoms and zero to 20 volume percent of an anhydride of such a perfluoro acid, based on the volume of the anhydride plus the perfluoro acid used;
    (c) as catalyst a Co(II) of Co(III) salt or an organic acid which is soluble in said solvent, said reaction being effected (1) under substantially anhydrous conditions and (2) at a temperature in the range zero to 50° C. when $H_2O_2$ or a peracid is the oxidant; and in the range 25°–150° C. when acetaldehyde plus molecular oxygen is the oxidant, thereby forming the phenyl ester of said perfluoromonocarboxylic acid.

2. A process of claim 1 wherein the oxidant is a mixture of acetaldehyde and molecular oxygen.

3. A process of any one of claim 2 wherein said acid of said solvent is perfluoroacetic acid.

* * * * *